United States Patent [19]

Pappas et al.

[11] Patent Number: 5,424,061
[45] Date of Patent: * Jun. 13, 1995

[54] QUICK-DRYING NAIL ENAMEL COMPOSITIONS AND METHOD FOR COATING A SURFACE

[75] Inventors: Dennis A. Pappas, New York, N.Y.; Harold J. Laresen, Wayne, N.J.

[73] Assignee: Amalia, Inc., New York, N.Y.

[*] Notice: The portion of the term of this patent subsequent to Mar. 3, 2009 has been disclaimed.

[21] Appl. No.: 175,306

[22] Filed: Dec. 29, 1993

Related U.S. Application Data

[60] Division of Ser. No. 816,768, Jan. 2, 1992, Pat. No. 5,275,807, which is a division of Ser. No. 452,618, Dec. 18, 1989, Pat. No. 5,093,108, which is a continuation-in-part of Ser. No. 311,479, Feb. 16, 1989, abandoned.

[51] Int. Cl.⁶ .............................................. A61K 7/04
[52] U.S. Cl. ..................................... 424/61; 424/401
[58] Field of Search ................................. 424/61, 401

[56] References Cited

U.S. PATENT DOCUMENTS

| | | | |
|---|---|---|---|
| 1,878,103 | 9/1932 | Bradley | 424/61 |
| 2,703,763 | 3/1955 | Marrian et al. | 424/61 |
| 4,421,881 | 12/1983 | Benkendorf et al. | 424/61 |

FOREIGN PATENT DOCUMENTS 724041  2/1955  United Kingdom.

OTHER PUBLICATIONS

*The Chemical Formulary*, vol. X, p. 66, Example No. 3, 19.
*Cosmetics*, vol. II, p. 167 (19).
*Harry's Cosmeticology*, pp. 374–387.
Wm. R. Keithler, *The Formulation of Cosmetics and Cosmetic Specialties*, pp. 439–447 (1956).

*Primary Examiner*—D. Gabrielle Phelan
*Attorney, Agent, or Firm*—Henry D. Coleman; R. Neil Sudol

[57] ABSTRACT

The present invention relates to novel, quick drying nail enamel compositions which dry in a period of time no greater than three minutes. The compositions of the present invention preferably dry in a period no greater than about two minutes and most preferably dry in a period no greater than about 90 seconds. Compositions drying in a period less than 60 seconds are especially preferred and are also described. The compositions of the present invention have acceptable static viscosities ranging from about 400 to about 1200 centipoises and may accommodate numerous pigments to produce nail enamel compositions exhibiting favorable characteristics, including acceptable durability and gloss.

20 Claims, No Drawings

QUICK-DRYING NAIL ENAMEL COMPOSITIONS AND METHOD FOR COATING A SURFACE

This is a division of application Ser. No. 07/816,768, filed Jan. 2, 1992, issued as U.S. Pat. No. 5,275,807 on Jan. 4, 1993, which is a division of Ser. No. 452,618, filed Dec. 18, 1989, now U.S. Pat. No. 5,093,108, issued Mar. 3, 1992, which is a continuation-in-part of U.S. Ser. No. 07/311,479, filed Feb. 16, 1989, now abandoned.

FIELD OF THE INVENTION

The present invention relates to novel, quick drying nail enamel compositions which dry in a period of time no greater than about three minutes. The compositions of the present invention preferably dry in a period of time no greater than about two minutes and most preferably dry in a period no greater than about 90 seconds. Compositions drying in a period less than 60 seconds are especially preferred and are also described. The compositions of the present invention have acceptable static viscosities ranging from about 400 to about 1200 centipoises and may accommodate numerous pigments to produce nail enamel compositions exhibiting favorable characteristics, including acceptable durability and gloss.

The compositions of the present invention comprise a primary film-forming polymer, a secondary film-forming polymer, for example, a resin which functions to strengthen the primary film-forming polymer and improve the adhesion and gloss of the nail enamel, a plasticizer and a solvent system containing a plurality of solvents one of which is acetone in an amount no less than about 4.5% and preferably no less than about 13% by weight of the composition. In particularly preferred compositions according to the present invention, acetone comprises about 15% to about 25% of the total weight of the composition. Preferably, the nail enamel compositions of the present invention contain a pigment for coloring the nail coating and a thixotropic agent, for example a clay such as a stearalkonium hectorite, in addition to other additives such as preservatives, stabilizers and fragrances.

BACKGROUND OF THE INVENTION

A large number of methods and compositions for beautifying and strengthening the nails of humans are well known. Prior art methods include coating the nail of an animal, including humans with a composition including a film-forming polymer and additional ingredients such as pigment, plasticizer and solvents or alternatively, attaching preformed artificial nails to human nails with adhesives. Additional methods include adding crosslinkable polymers to nail coating compositions to mend, strengthen and elongate natural nails and repairing nails with a fabric patch.

Most nail enamel compositions presently on the market or disclosed in the prior art dry in five minutes or longer. Even those nail enamels that claim to be quick-dry, i.e., dry in about five minutes are often not truly dry but rather are only dry to the touch. When a purportedly "dry" nail enamel of the prior art brushes up against a hard surface, the nail enamel often smudges, leaving tack.

One nail polish drying composition disclosed in U.S. Pat. No. 4,798,720 prepared from commercially available top coat nail polish, acrylic nail powder, acrylic nail primer and the adhesive "crazy glue" is described as being used in combination with commercially available colored nail polishes to alter the drying time of the nail polish to a period of more than three minutes. The compositions of this patent are used as base coats in combination with commercially available pigment containing nail polishes. The patent claims to dry from one to seven coats of pigment containing nail polish within a period ranging from about three to five minutes. This composition functions as a base coat or top coat and unlike the composition of the present invention, must be used in combination with a commerically available pigment nail polish to provide a lasting pigmented nail enamel finish.

A nail polish which can be used to coat a natural or synthetic nail which dries in less than three minutes without requiring an additional application of a base coat or top coat would be very desirable. Nail polishes which dry in a period of less than 150 seconds would be even more desirable, as would polishes that dry in periods less than about 90 seconds. A nail polish composition which would dry in a period of no greater than about 60 seconds would be especially useful in situations where "drying" time is important.

Working women need to have a product which can be easily applied and which dries in the shortest amount of time to avoid a situation where they are simply wasting precious time waiting for their nail polish to dry. In the manicure and pedicure industries, a colored nail polish composition which can dry in a period less than three minutes would provide a significant advantage over the prior art compositions.

Solvent mixtures for nail enamels of the prior art have covered a wide range of compositions and have included as many as six or seven solvents to control flow, viscosity, evaporation rate and drying time of the enamel. As discussed in Peirano, "Nail Lacquers and Removers", *Cosmetics Science and Technology*, Interscience Publishers, Inc., 1957, solvent or mixed solvents used as the volatile portion of nail enamels are of prime importance because of their direct effect on ease of application of enamel, on the rate of drying and hardening, on the viscosity of the enamels and on the characteristics of the final film. According to this reference, too rapid a rate of evaporation causes a poor flow of the enamel and also gives an uneven, streaky application. The reference also cites the importance of proper solvent balance during the drying stages of the lacquer. In general, due to the wide differences in evaporation rates of the solvents which are included in the prior art compositions, these compositions undergo many changes during the drying of the film. For example, during the course of evaporation of the solvent from the nail enamel on the nail, differential evaporation of the solvents within the composition may result in the presence of higher concentrations of certain solvents during drying, which in turn creates precipitation of the film forming polymer, resin and/or plasticizer, thereby destroying the integrity of the film and the appearance of the enamel. If the solvent becomes too lean to maintain the solubility of the resin in solution, the resin will precipitate, also resulting in unacceptable results.

The complicated character of the nail enamel mixtures of the prior art and the many possible combinations of volatile and nonvolatile components had, until the unexpected discovery of the present invention, made the determination of a proper solvent balance from the perspective of viscosity, solubility of the individual components and the acceptability of the deposited enamel (gloss) in combination with a drying time of less than three minutes virtually impossible. Until the discovery of the present invention, the identification of the evaporation rates of the individual solvents under various conditions had not removed the uncertainty involved in determining a suitable solvent balance incorporating quick-drying characteristics. Although the desirability of a quick drying nail enamel has been a long-felt need, the rate of drying of the nail enamels of the prior art has been limited by the aforementioned considerations. Thus, before the discovery of the present invention, simply incorporating low boiling solvents did not increase the likelihood that an acceptable solvent system for nail enamels would be found or that one could obtain a nail enamel composition which dried in under three minutes. In the present invention, the use of acetone in certain weight percentages of the composition, in combination with numerous solvents which provide acceptable viscosity, creates a consistent quick-drying solvent system which provides the nail enamel with favorable characteristics of drying time, viscosity, gloss, flexibility and durability.

Acetone, also known as 2-propanone, dimethylketone and beta-ketopropane is a volatile solvent which has a boiling point of 56.5° C. and is miscible with an extremely large number of solvents including water, alcohol, dimethylformamide, chloroform, methylene chloride, toluene, esters, including methylacetate and ethylacetate, benzene and toluene, ethers and numerous oils and hydrocarbons, among others. The uniqueness of acetone for use in the present invention resides in the fact that acetone will interact with solvents used in nail enamels to produce a solvent system which evaporates in under three minutes.

It has surprisingly been discovered that the inclusion of specific weight percentages of acetone in combination with additional solvents in compositions for coating natural and synthetic nails produces a nail coating composition which dries in a period of time less than three minutes and produces a coating on a nail which is hard, flexible and has good wear characteristics including durability and high gloss. Moreover, the use of acetone in the volatile component of nail enamel compositions of the present invention within specific weight percentages provides a consistent basis upon which one of ordinary skill in the art may add additional solvents without dramatically adversely affecting the drying time of the nail enamel.

OBJECTS OF THE PRESENT INVENTION

It is therefore an object of the present invention to provide a pigmented nail polish composition which can be applied to natural and synthetic nails and will dry in a period less than 3 minutes, preferably less than two minutes, most preferably less than 90 seconds and especially less than 60 seconds, an a clear nail enamel which can also be used as a basecoat or top coat which dries in less than 30 seconds.

It is a further object of the present invention to provide a general method for making nail polish formulations which will dry in a period less than three minutes.

It is still another object of the present invention to provide a nail preparation kit comprising a base adapted for forming a coating on a natural or synthetic nail and a suitable solvent system which together will provide a coating of nail enamel which dries in a period less than three minutes.

It is still a further object of the present invention to provide a novel method for coating nails with a pigmented nail polish composition which dries in a period less than three minutes, preferably less than two minutes, most preferably less than 90 seconds and especially less than 60 seconds, and a clear nail enamel which can also be used as a basecoat or top coat which dries in less than 30 seconds.

It is yet additional object of the present invention to provide a number of solvent systems which may be added to standard nail polish formulations to substantially hasten the drying of a nail enamel composition to a durable, hard finish exhibiting high gloss without adversely affecting the beneficial characteristics of the complete nail polish formulation.

These and other objects of the present invention may be readily determined from the detailed description of the invention which is set forth herein.

BRIEF DESCRIPTION OF THE INVENTION

In accordance with the objects of the present invention there is provided a nail enamel preparation comprising a fluid mixture adapted for drying and hardening to form a coating on a nail. The fluid mixture comprises, in part, a plurality of solvents, one of which is acetone. In nail enamel compositions according to the present invention, acetone comprises about 4.5% to about 35% by weight. It has surprisingly been discovered that acetone will interact with any number of solvents within a nail coating composition to produce a composition which will dry within a period of time significantly shorter than would be expected from the evaporation rates of the individual solvents.

The present invention therefore relates to novel compositions for coating natural and synthetic nails which dry to a hard, flexible coating exhibiting favorable characteristics of durability and high gloss comprising:

a) a primary film-forming polymer;
b) a secondary film-forming polymer;
c) at least one plasticizer;
d) at least one thixotropic agent;
e) at least one pigment; and
f) an amount of acetone ranging from about 4.5% to about 35% by weight of said composition in combination with at least one additional solvent having sufficient polarity in combination with acetone to dissolve said primary and secondary film-forming polymers and said plasticizer to produce a stable composition having a static viscosity ranging from about 400 to about 1200 centipoises, said composition drying on a natural or synthetic nail surface within a period of time less than three minutes.

In addition to the components set forth above, the compositions of the present invention may further comprise additional agents, for example, fragrances and preservatives.

It is a surprising result that the nail enamel compositions embraced by the present invention which include significant quantities of solvents which include acetone and which have a static viscosity of about 400 to about 1200 centipoises, optimally, about 800 centipoises, consistently dry in less than three minutes. It is particularly surprising that the inclusion of certain weight percentages of acetone in combination with numerous solvents which do not otherwise dry within a period less than three minutes will produce nail enamel compositions which will dry in a period of time less than three minutes, for example, two and a half minutes, 90 seconds or even less than 1 minute. In certain particularly preferred compositions according to the present invention which do not include thioxotropic agents and pigments, an especially fast drying base coat or top coat formulation is presented comprising about 18% to about 35% by weight acetone, preferably about 24% to about 35% by weight acetone, in combination with other solvents, primary film-forming polymer, secondary film-forming polymer and at least one plasticizer. Such compositions, which can be used as base coats, top coats or clear enamels, dry in a period of time less than about 30 seconds.

It is also surprising that the solvent combinations which are used in the compositions of the present invention dry in such a short period of time in a uniform fashion without streaking or precipitation of the solid material. The resulting enamel coat is uniform, hard and flexible and exhibits favorable durability and high gloss.

In accordance with the present invention, the nail enamel compositions of the present invention include a primary film-forming polymer. The primary film-forming polymer is used as the base material for the nail enamel. In the present invention numerous film-forming polymers may be used as the primary film-forming polymer including cellulose acetate, cellulose acetate-butyrate, ethyl cellulose, numerous vinyl polymers as well as a number of methacrylate and acrylate type polymers. Preferably, nitrocellulose is used as the film-forming polymer in the present invention.

In addition to the primary film-forming polymer, the compositions of the present invention also include an amount of a secondary film-forming polymer effective to strengthen the primary film-forming polymer and provide the enamel coating with acceptable gloss and adhesion characteristics. Exemplary secondary film-forming polymers or resins which may be used in the present invention include, for example, drying and non-drying alkyd resin, polyvinyl resins, for example polyvinyl acetate, polyester resins, acrylic and methacrylic resins and arylsulfonamide-formaldehyde resins, for example toluene sulfonamide-formaldehyde resin. These secondary film-forming polymers are added to the primary film-forming polymers of the present invention to strengthen and add acceptable wear characteristics to the primary film-forming polymer. Toluene sulfonamide-formaldehyde resin, a condensation product of formaldehyde and toluene sulfonamide is especially preferred for use as a secondary film-forming polymer in the present invention.

In addition to the primary and secondary film-forming polymers the compositions according to the present invention also comprise at least one plasticizer, preferably for example, dibutyl phthalate and most preferably a mixture of dibutyl phthalate and camphor to add characteristics of flexibility to the nail coating. Certain secondary film-forming polymers, for example, toluene sulfonamide/epoxy resin and toluene sulfonamide/epoxy resin butyl acetate, available from Telechemische, Newburgh, N.Y., which have acceptable plasticization characteristics may be used in certain embodiments of the present invention without the need to include a separate plasticizer.

In addition to the above-described components, the compositions of the present invention may additionally comprise a clay thixotropic agent, for example, stearalkonium hectorite, for example, the Bentones ™, available from NL Industries, New Jersey, USA and in addition a coloring substance or pigment to give the preparation a cosmetically acceptable shade and to opacify the film.

In addition to the components set forth above, the compositions of the present invention may also include further additives including stabilizers, preservatives, fragrances and antioxidants.

To provide acceptable static viscosities within the range of about 400 to 1000 centipoises, the nail enamel compositions of the present invention generally comprise about 50% to about 75% by weight solvent, preferably about 60% to about 70% by weight solvent, and most preferably about 64% to about 68% by weight solvent.

In addition to the disclosed weight percentages of acetone which are used in the present invention, other exemplary solvents include for example, ethyl acetate, methyl acetate, methanol, ethanol, isopropanol, n-butanol, n-butyl acetate, methylchloroform, methylene chloride, toluene, xylene, additional aromatic (containing phenyl groups) solvents and mixtures thereof, among others, including amyl acetate, numerous ethers, numerous ketones including methylethylketone and alkanes including pentane, cyclopentane, hexane, and cyclohexane, among others, in varying weight percentages. In addition to the above-named solvents, other solvents which may be used in the present invention include, for example, cyclic ethers such as tetrahydrofuran and 1,4-dioxane, among others. High boiling solvents, for example, cellosolve, butyl cellosolve acetate, cellosolve acetate, methyl cellosolve acetate, butyl cellosolve, ethyl cellosolve and phenylated solvents including xylene may also be used. Of course, these high-boiling solvents, because of their tendency to increase drying times are included in weight percentages in compositions of the present invention in amounts consistent with producing a nail composition which dries in less than three minutes. One of ordinary skill in the art will know to vary the weight percentages of acetone and the other solvents used in compositions of the present invention within the teachings of the present invention to produce a large number of acceptable solvent combinations for use in nail enamel compositions which dry in a period of less than three minutes.

In the present invention, it has been found advantageous to include acetone in amounts ranging from about 4.5% to about 35%, preferably about 13% to about 30% and most preferably about 15% to about 25% by weight acetone. In certain embodiments of the present invention in which pigment and the thixotropic agent Bentone RSNC ™ is included, about 18% by weight acetone has been found to be quite advantageous.

In addition to acetone, the present invention may also include an alcohol, for example, ethanol, isopropanol, methanol or n-butanol in amounts generally less than 10% and preferably less than about 5% by weight of the nail enamel composition. The compositions of the present invention also generally include an ester, preferably an ester of acetic acid such as methyl acetate, ethyl acetate, propyl acetate, n-butyl acetate and mixtures of these esters in amounts ranging up to about 50% by weight of the nail enamel compositions, and preferably about 20% to about 30% by weight of the nail enamel compositions.

Compositions of the present invention may also include an aromatic diluent, for example, toluene, xylene and certain naphtha derivatives. Because of the regulatory implications of using certain of these solvents, a number of substitutes for toluene may be included in compositions of the present invention. Substitutes for toluene include for example, esters of acetic acid such as methyl acetate, ethyl acetate and n-butyl acetate, chlorinated hydrocarbons, for example, methylene chloride, methylchloroform, various ketones other than acetone including methylethyl ketone and various hydrocarbons including hexane, cyclohexane and pentane, among others.

It is an especially surprising result that acetone in an amount ranging from about 4.5% to about 35% by weight of the final composition in combination with a solvent combination which otherwise does not dry or evaporate within a period of three minutes on a human or artificial nail will dry in a time period less than three minutes. The solvents which are included with acetone in the present invention are chosen for their ability, in combination with acetone, to dissolve the primary film-forming polymer, the secondary film-forming polymer and the plasticizer and for their ability to provide a final static viscosity in combination with the solids of the compositions of the present invention including pigment and thixotropic agent in the range of about 400 to about 1200 centipoises, preferably about 800 centipoises.

The present invention also relates to a nail preparation kit comprising a polymer base adapted for drying and hardening to form a pigmented coating on a nail upon mixture of the base with a suitable solvent mixture, the solvent mixture comprising an amount of acetone comprising at least about 4.5% to about 35% by weight of the final nail enamel composition including solids in combination with a plurality of solvents which, include acetone and which dissolve a primary film-forming polymer, a secondary film-forming polymer and a plasticizer, the composition having a final static viscosity ranging from about 400 to about 1200 centipoises, preferably about 800 centipoises. In addition to primary film-forming polymer, secondary film-forming polymer and plasticizer, the polymer base additionally comprises a thixotropic agent and at least one pigment and optionally, additional additives including preservatives and fragrances, among others. In this nail preparation kit aspect of the present invention, the polymer base comprises about 25% to about 50% by weight of the final nail enamel composition to be applied to the nail and the solvents comprise about 50% to about 75% by weight of the composition, preferably about 60% to about 70% by weight and most preferably about 64% to about 68% by weight solvent. The nail preparation kit of the present invention also includes top coat, basecoat and clear nail enamel compositions which contain at least about 18% to about 35% by weight acetone, preferably at least about 24% to about 35% by weight acetone and an absence of pigment and thixotropic agent. These compositions dry in a period of time no greater than about 30 seconds.

In still another aspect of the present invention, solvent mixtures particularly adapted for use in combination with pigmented polymer bases for use in nail enamel compositions are also disclosed. In this aspect of the present invention, a solvent mixture comprises acetone in an amount equal to about 6% to about 70% by weight of the solvent mixture and at least one additional solvent to produce a solvent mixture which, in combination with a polymer base adapted for use in pigmented nail enamel preparations, provides a nail enamel preparation containing at least about 4.5% to about 35% by weight acetone, said nail enamel composition having a static viscosity ranging from about 400 to about 1200 centipoises and drying in a period less than three minutes to a hard, flexible pigmented surface having acceptable wear characteristics including durability and high gloss. Solvent systems for use in basecoat, top coat and clear enamel compositions contain at least about 24% by weight acetone up to about 70% by weight acetone.

In accordance with a further aspect of the present invention, the present invention includes a process for making the pigmented nail enamel compositions of the present invention. In this aspect of the present invention nail enamel compositions of the present invention are formulated by first mixing a number of solvents including an amount of acetone equal to about 6% to about 70% by weight of the solvent mixture to produce a solvent mixture. Thereafter, a primary film-forming polymer, a secondary film-forming polymer and at least one plasticizer is added stepwise in any order in conjunction with vigorous mixing, until a viscous solution is produced. The compositions produced according to this method can be used as colorless nail polishes or alternatively, as base coat and top coat formulations in conjunction with colored nail polishes. After the viscous solution is produced, a thixotropic agent, for example, stearalkonium hectorite, is added to the above-described mixture in conjunction with vigorous stirring (under strong shearing force with a Hoffmeyer industrial mixer) generally for a period of about at least one hour to produce a gelled mixture. In the last step, one or more pigments are added to the above gelled mixture to produce the rapid drying mixtures according to the present invention. The final composition produced by the method according to the present invention obtains a final static viscosity ranging from about 400 to about 1200 centipoises.

While it is possible to produce the compositions of the present invention following the general procedures of the method aspect of the present invention, it is clearly preferred that all mixing of the nail enamel compositions and especially those containing stearalkonium hectorite thixotropic agent and pigment, be performed under high shear speed. Therefore, one of the more important aspects of the method of the present invention includes the use of vigorous stirring at high shear speed, for example using a Hoffmeyer industrial mixer for a period of time sufficient to produce a thixotropic gel, generally at least about one hour and preferably at least about two hours.

DETAILED DESCRIPTION OF THE INVENTION

Compositions of the present invention for coating a natural or synthetic nail comprise the following ingredients:

a) a primary film-forming polymer;
b) a secondary film-forming polymer;
c) at least one plasticizer;
d) at least one thixotropic agent;
e) at least one pigment; and
f) an amount of acetone ranging from about 4.5% to about 35% by weight of said composition in combination with at least one additional solvent having sufficient polarity in combination with said acetone to dissolve said primary and secondary film-forming polymers and said plasticizer to produce a stable composition having a static viscosity ranging from about 400 to about 1200 centipoises, said composition drying on a natural or synthetic nail within a period of less than three minutes.

In certain embodiments, the compositions according to the present invention contain an absence of thixotropic agent and pigment and contain at least about 18% by weight acetone, preferably at least about 24% by weight acetone so that the drying time is less than about 30 seconds. These compositions may be used as clear nail enamel or alternatively as base coats or top coats for application to nails.

In addition to the above components, the compositions according to the present invention may further comprise one or more additional agents, for example, stabilizers, fragrances, anti-oxidants and preservatives.

The compositions of the present invention contain a primary film-forming polymer for example, cellulose acetate, cellulose acetate-butyrate, ethyl cellulose, numerous vinyl polymers as well as a number of methacrylate and acrylate type polymers. The preferred primary film-former for use in the present invention is nitrocellulose. Nitrocellulose for nail enamel compositions of the present invention is of two standard types designated respectively, RS and SS. RS nitrocellulose, available from a number of manufacturers including S.N.P.E. of Bergerac, France and Hercules Inc., of Philadelphia, Pa., USA, the preferred nitrocellulose, is available in a wide range of viscosities. Although a number of different nitrocellulose film-formers may be used in compositions of the present invention, it is preferred that nitrocellulose RS ½ second, available from Hercules be used in the compositions of the present invention. In general, the primary film-forming polymer is included in compositions of the present invention in amounts effective to provide toughness, hardness, resistance to abrasion and its solvent release and a film thickness, in combination with secondary film-forming polymers and plasticizers of about 2.5 mil to 6 mil, preferably about 3 mil. In general, the amount of primary film-forming polymer comprises about 5% to about 25% by weight of the compositions, preferably about 9.0% to about 20% by weight of the compositions and most preferably about 10% to about 15% by weight of the composition.

In addition to the primary film-forming polymer, the compositions of the present invention also include a secondary film-forming polymer which is added to the primary film-forming polymer for its ability to provide strength, gloss and adhesion. Exemplary secondary film-forming polymers which may be used in the present invention include alkyd resins (both drying and non-drying), polyvinyl resins, for example, polyvinyl acetate, polyester resins, acrylic and methacrylic resins and arylsulfonamide-formaldehyde resins. Toluene sulfonamide-formaldehyde resin, a condensation product of formaldehyde and toluene sulfonamide is especially preferred for use as a secondary film-forming polymer in the present invention. In general, the amount of secondary film-forming polymer used is that amount effective to strengthen the primary film-forming polymer and provide an effective gloss and adhesion. One of ordinary skill in the art will be able to determine the amount of secondary film-forming polymer which may be added to the compositions of the present invention to produce the desired effect without engaging in undue experimentation. However, in general, the amount of secondary film-forming polymer to be used in the present invention ranges from about 4.0% to about 13% by weight of the composition, preferably about 7.0% to about 10% by weight and most preferably about 9.0% by weight of the composition.

In addition to primary and secondary film-forming polymers, the compositions according to the present invention also include at least one plasticizer. Plasticizers for use in the present invention are added to soften and plasticize the primary film-forming polymer. The choice of plasticizer for a nail enamel composition may vary as a function of the color, odor, effect on viscosity of the enamel, effect on the drying rate, the amount needed to meet flexibility requirements, the volatility of the plasticizer and compatability with the other components of the compositions. Plasticizers for use in the present invention include tricresyl phosphate, diamylphthalate, dibutyl phthalate, diethyl phthalate, dibutyl tartrate, benzyl benzoate, tributyl phosphate, butyl acetyl ricinoleate, butyl glycolate, dioctyl phtalate, butyl stearate, triphenyl phosphate, triethyl citrate, camphor, castor oil and dibutoxy ethylphthalate, among others. Preferred plasticizers for use in the present invention include dibutyl phthalate, camphor and especially mixtures of dibutyl phthalate and camphor. In general, plasticizer is included in the compositions of the present invention in an amount sufficient to provide acceptable flexibility to nail enamel on the human or synthetic nail surface. By acceptable flexibility, we mean that the composition will evidence no cracking when a 6 mil film which has been dried on an aluminum strip surface for at least two hours is bent around a 0.25" mandrel (available from Gardner Corporation, Florida, USA). In general, the amount of plasticizer for use in the compositions of the present invention ranges from about 2.0% to about 7.5%, preferably about 3.0% to about 6.0% and most preferably about 3.5 to about 5.5% by weight.

In addition to the primary and secondary film-forming polymers and plasticizer, the compositions according to the present invention also include a solvent mixture containing acetone in an amount ranging from about 6.0% to about 70% of the total weight of the solvent. Because the total amount of solvent ranges from about 50% to about 75% by weight of the nail enamel compositions of the present invention, acetone therefore comprises about 4.5% to about 35% by weight of the total weight of the nail enamel compositions. The amount of acetone included in the compositions is selected to create an interaction with the other solvents that are used in the compositions. It has surprisingly been found that acetone used in combination with additional solvents will result in a nail enamel composition which will dry in less than three minutes. By "dry" we mean that the nail enamel compositions will evidence no tack with a cotton swab ("Q-tip") when drawn down on to a 3 mil thick layer on lineta cards (Lineta Company, Hohokus, N.J.) at room temperature and a relative humidity of about 50 to 55%. Of course, the drying time of a nail enamel formulation will vary as a function of the temperature and relative humidity of the ambient atmosphere.

Other solvents which may be used in the compositions of the present invention include, for example, ethyl acetate, methanol, ethanol, isopropanol, n-butanol, n-butyl acetate, methyl chloroform, methylene chloride, toluene and mixtures thereof, among others, including amyl acetate, numerous ethers, and alkanes including pentane, hexane, and cyclohexane and mixtures thereof among others, in varying weight percentages. In addition to the above-named solvents, other solvents may be used in the present invention include, for example, methyl acetate, cyclopentane and tetrahydrofuran, including mixtures thereof, among others. High boiling solvents, for example, cellosolve, butyl cellosolve acetate, cellosolve acetate, methyl cellosolve acetate, butyl cellosolve, ethyl cellosolve and phenylated solvents including xylene may also be used.

Of course, the high-boiling solvents, have a tendency to increase drying times and therefore are included in weight percentages in compositions of the present invention in amounts consistent with producing a nail composition which dries in less than three minutes. In many cases, the amount of high boiling solvent is included in an amount no greater than about 5.0% and often in an amount significantly less than about 5% by weight of the final composition. One of ordinary skill in the art will know to vary the weight percentages of acetone and the other solvents used in compositions of the present invention within the teachings of the present invention to produce a large number of acceptable solvent combinations for use in nail enamel compositions which dry in a period of less than three minutes.

In addition to acetone, the inclusion of methylchloroform in compositions of the present invention in many cases may have a beneficial effect on the drying time. However, the effect of methylchloroform is not nearly as great as that caused by the disclosed weight percentages of acetone.

While not being limited by way of theory, it is believed that acetone is responsible for creating an interaction with the other solvents utilized in the present invention to substantially reduce the drying times of nail compositions to below three minutes. Such interaction may be due to the universality of solvency that acetone displays with almost any solvent. It is quite surprising that a combination of solvents which, in combination with the non-volatile components of the present invention, normally do not dry within a period even close to three minutes, dries in a period under three minutes. Even more surprising is the fact that the inclusion of at least about 18% by weight acetone in combination with other solvents will produce a pigmented nail enamel composition which will dry within about 60 seconds and a clear nail enamel composition containing an absence of pigment and thixotropic agent which dries in less than 30 seconds.

The amount of acetone included within the compositions according to the present invention varies between about 4.5% and about 35%. This range represents a guideline for inclusion of acetone in compositions according to the present invention. The lower limit of this range represents the least amount of acetone that is generally used to produce a nail enamel which dries in less than three minutes. The upper limit of this range represents the amount of acetone above which begins to produce an unacceptable streaking effect on the enamel during coating. Compositions according to the present invention include an amount of acetone generally falling within this range, the amount of acetone to be included being determined by the desired drying time and the additional solvents which are added to produce the desired viscosity and flow characteristics.

In many of the commercial nail enamel preparations on the market, toluene, xylene or other aromatic solvent is included in varying amounts as a diluent. In an additional aspect, the present invention also relates to quick-drying compositions which have acceptable characteristics and which exclude toluene and other aromatic solvents which may not be acceptable for inclusion in cosmetic formulations by regulatory agencies. In this aspect of the present invention, toluene or other aromatic solvent is replaced with another solvent, especially for example, a ketone-containing composition other than acetone such as methyl ethyl ketone, one of the esters of acetic acid such as ethyl acetate or methyl acetate, chlorinated hydrocarbons for example, methylchloroform, methylene chloride, chloroform and other solvents, for example, hexane, cyclohexane, pentane and heptane, as well as numerous additional solvents.

In compositions of the present invention which contain an absence of pigment and thixotropic agents, virtually any low boiling solvent, i.e., a solvent which has a boiling point less than about 90° C. may be substituted for toluene or other aromatic (containing a phenyl group) solvent provided that the primary film-forming polymer, secondary film-forming polymer and plasticizer are placed in solution. In compositions without thixotropic agent or pigment, numerous high boiling solvents may also be used, but care must be taken to limit the use of such solvents to low levels to avoid increasing the drying time above acceptable limits. An acceptable drying time for compositions which contain an absence of pigment and/or thixotropic agent is less than 30 seconds. In order to produce such a fast drying time, in this aspect of the present invention, these nail enamel compositions, contain at least 18% by weight acetone and preferably at least about 24% acetone. Following the guidelines and descriptions of the present application will enable one of ordinary skill in the art to readily substitute for toluene and still maintain the drying times within acceptable limits.

In compositions of the present invention which contain a pigment and preferably, a thixotropic agent, the choice of solvents which may substitute for the toluene or other aromatic diluent is more limited. In these compositions, care must be taken to substitute a solvent having similar polarity to toluene. Because the use of thixotropic agent in preferred compositions of the present invention is often advantageous and because the use of thixotropic agent may be affected by the polarity of the solvents chosen, care must be taken when substituting for toluene in compositions according to this aspect of the present invention. In certain cases, the use of very large quantities of non-polar solvents, for example, hydrocarbons such as hexane, heptane and pentane as well as other non-polar solvents, without the inclusion of sufficient amounts of more polar solvents, may affect the ability of the thixotropic agent to form a gel, preferably a colloidal gel. In addition, the inclusion of large percentages of highly polar solvents, for example, methanol, ethanol and isopropanol may adversely affect the ability of the thixotropic agent to form a gel, preferably a colloidal gel. Therefore, polar substitutes for toluene in this aspect of the present invention should be limited to no greater than about 25% by weight of the total weight of the composition and preferably no greater than about 18% by weight of the composition. Preferably, substitutes for toluene in this aspect of the present invention include esters of acetic acid, for example methyl acetate, ethyl acetate and n-butyl acetate, ketones other than acetone, including methyl ethyl ketone, chlorinated hydrocarbons, for example, methylene chloride, chloroform and methylchloroform as well as other solvents of similar polarity to toluene.

In certain compositions according to the present invention, a pigment and a thixotropic agent is also added.

Pigments are added to the compositions to provide cosmetically acceptable shades and to opacify the films. Pigments for use in the present invention include for example red pigments, including for example, D & C red Nos. 10, 11, 12 and 13, D & C red No. 7, TOB-BON maroon (D & C red No. 34). Other pigments which may be used in compositions according to the present invention include the Lake pigments, for example, D & C yellow No. 5 Lake, D & C Red No. 2 Lake, and Ext. D & C Red No. 2 Lake. In addition to the above-named pigments, additional pigments can include cosmetic-grade or purified titanium dioxide (white), yellow and red iron oxides, iron blue, iron black, ultramarine blue, chromide oxide greens, carbon black or lampblack (generally, in minute quantities).

In addition to the above-named pigments, iridescent additives may be included for example, "pearl essence", which is a suspension of crystalline guanine in nitrocellulose and solvents as well as other additives which will affect the appearance of the pigment. Although the amount of pigment in compositions of the present invention will vary as a function of the type of pigment and other components included in the compositions, in general, pigments are included in an amount ranging from about 0.025 to about 4.0% by weight and preferably in an amount ranging from about 0.5 to about 1% by weight of the composition.

When pigments are included in compositions according to the present invention, it is useful to include a thixotropic agent for enhancing the suspension of pigment in the other components of the composition. Although a number of thixotropic agents generally used in the nail enamel art may be used to produce compositions according to the present invention, preferred thixotropic agents include the thixotropic clays, especially stearalkonium hectorites. Particularly preferred stearalkonium hectorites for use in the present invention include the Bentones TM, including Bentone 27 TM, available from NL Industries, New Jersey, USA. An especially preferred stearalkonium hectorite containing thixotropic agent for use in the present invention is Bentone RSNC TM, available from Penn Color, Doylestown, Pa. USA. Bentone RSNC TM is a composition containing about 25% by weight stearalkonium hectorite milled to about 5 microns in nitrocellulose and plasticizer (camphor). In particularly preferred compositions according to the present invention, thixotropic agent is included in an amount sufficient to produce a gel, preferably a colloidal gel. In general, the pure thixotropic agent without the additives, is included in amounts ranging from about 2% to about 5% by weight of the composition, preferably about 2 to about 4% and most preferably about 2 to 3% by weight of the composition.

The use of a preferred thixotropic agent, especially Bentone RSNC TM in combination with pigment for use in compositions of the present invention in combination with a sufficiently polar solvent mixture and mixing under shearing force (Hoffmeyer industrial mixer for a period of at least one hour, preferably two hours) results in a gel which serves to suspend the pigment and maintain the pigment in suspension for extended periods of storage. In this aspect of the present invention, compositions according to the present invention include Bentone RSNC TM in sufficient quantity to produce a gel are storage stable, i.e., they maintain their viscosity, consistency and pigment in suspension without the need for significant shaking even after extended periods of storage.

It is important to note that the acetone-containing solvent mixtures chosen for use in compositions according to the present invention which contain this thixotropic agent should be of sufficient polarity to favorably interact with the stearalkonium hectorite to produce a gel. The gel which is produced in preferred embodiments of the present invention results in a suspension of pigment which will not settle to the same extent as nail enamel compositions which do not contain such a gel suspension. The compositions of the present invention which utilize stearalkonium hectorite thixotropic agents are therefore storage stable and may be applied to the nail even after periods of long storage by a simple shaking of the container before application. There is no need to include for example, a steel ball to enable a vigorous shaking of the composition before application as is required by many of the compositions of the prior art.

In addition to the above-described components, the compositions of the present invention may also include additional additives including stabilizers, preservatives, anti-oxidants and fragrances, depending upon the intended result. These components are well known in the art and may be included in amounts well within the teachings of the art.

The nail enamel compositions of the present invention have characteristics of quick-drying, flexibility, durability, adequate viscosity and high gloss. The pigmented compositions of the present invention dry in a period of less than three minutes. By "dry" we mean that the compositions will evidence no tack (absence of smudging) after a three minute drying period at room temperature and a relative humidity of 50-55%. Compositions of the present invention are also flexible, i.e., the composition will evidence no cracking when a 6 mil film which has been dried on an aluminum strip surface for at least two hours is bent around a 0.25" mandrel (available from Gardner Corporation, Florida, USA). Compositions of the present invention are also durable and do not chip or crack for a period of at least about three days of wearing on a human or synthetic nail.

The viscosities of compositions of the present invention are commercially acceptable. In general as previously indicated, the static viscosities of the compositions of the present invention fall within the range of about 400 to about 1200 centipoises, preferably about 800 centipoises. For purposes of defining the present invention, static viscosities are determined on a Brookfield RVF viscometer after at least 24 hours of incubation at 25° C. using a spindle #3 at 25° C. and 20 RPM. In addition to static viscosities, shaken viscosities are also generally commercially acceptable. Shaken viscosities differ from static viscosities and are determined in the following two ways. First, shaken viscosities are determined using a Brookfield LVF viscometer, spindle #3 at 60 RPM after the compositions are shaken for a brief period. The compositions of the present invention exhibit a shaken viscosity under these conditions generally ranging from about 250 to about 500 centipoises, with an optimum of about 400 centipoises. Additional shaken viscosities are determined at 6 RPM on a Brookfield LVF viscometer, spindle #3 at 25° C. Viscosities of the compositions of the present invention under these conditions generally range from about 800 to about 1200 centipoises, with an optimum of about 1000 centipoises.

Compositions of the present invention generally exhibit an acceptable gloss ranging from about 70 to about 95% reflection of light as determined by a Glossguard Meter (6 mil thick coating on an aluminum surface). Preferably, the compositions of the present invention exhibit a gloss ranging from about 85 to about 95% reflection of light as determined by a Glossguard Meter.

The present invention also relates to a nail preparation kit comprising a polymer base adapted for drying and hardening to form a pigmented coating on a nail upon mixture of the base with a suitable solvent mixture, the solvent mixture comprising an amount of acetone comprising at least about 4.5% to about 35% by weight of the final nail enamel composition including solids in combination with a plurality of solvents which, in combination with acetone dissolve the primary film-forming polymer, the secondary film-forming polymer and the plasticizer, the composition having a final static viscosity ranging from about 400 to about 1200 centipoises, preferably about 800 centipoises. In addition to primary film-forming polymer, secondary film-forming polymer and plasticizer, the polymer base additionally comprises a thixotropic agent and at least one pigment and optionally, additional additives including preservatives and fragrances, among others. In this nail preparation kit aspect of the present invention, the polymer base comprises about 25% to about 50% by weight of the final nail enamel composition to be applied to the nail and the solvents comprise about 50% to about 75% by weight of the composition, preferably about 60% to about 70% by weight and most preferably about 64% to about 68% by weight solvent. The nail preparation kit of the present invention also includes top coat, basecoat and clear nail enamel compositions which contain at least about 18% to about 35% by weight acetone, preferably at least about 24% to about 35% by weight acetone and an absence of pigment and thixotropic agent. These compositions dry in a period of time no greater than about 30 seconds.

To use the nail preparation kit of the present invention, the user will add the solvent mixture to the base formula which contains primary film-forming polymer, secondary film-forming polymer and plasticizer. After thoroughly mixing the solvent with the three solid ingredients, the resulting mixture may be used a basecoat, top coat, or clear nail enamel. Alternatively, if a pigmented nail enamel composition is desired, after thorough mixing of the solvent, primary film-forming polymer, secondary film-forming polymer and plasticizer, thixotropic agent is added and the mixture vigorously shaken for a period of time sufficient to produce a homogeneous mixture. Thereafter, pigment is introduced into the mixture and the pigment-containing mixture is thoroughly mixed until a homogeneous mixture is realized. The final product may then be stored or coated onto a natural or synthetic nail surface.

In still another aspect of the present invention, solvent mixtures particularly adapted for use in combination with pigmented polymer bases for use in nail enamel compositions are also disclosed. In this aspect of the present invention, a solvent mixture comprises acetone in an amount equal to about 6% to about 70% by weight of the solvent mixture and at least one additional solvent having a polarity sufficient to produce a solvent mixture which, in combination with a polymer base adapted for use in nail enamel preparations comprising a primary, film-forming polymer, a secondary film-forming polymer, at least one plasticizer, a thioxotropic agent and pigment, provides a nail enamel preparation containing at least about 4.5% to about 35% by weight acetone having a static viscosity ranging from about 400 to about 1200 centipoises and drying in a period less than three minutes to a hard, flexible pigmented surface having acceptable wear characteristics including durability and high gloss. Solvent systems for use in basecoat, top coat and clear enamel compositions contain at least about 24% by weight acetone up to about 70% by weight acetone.

The present invention also relates to methods of making the compositions of the present invention. In this aspect of the present invention nail enamel compositions of the present invention are formulated by first mixing a number of solvents including an amount of acetone equal to about 6% to about 70% by weight of the solvent mixture to produce a solvent mixture. Thereafter, a primary film-forming polymer, a secondary film-forming polymer and at least one plasticizer is added step-wise in any order in conjunction with vigorous mixing until a viscous solution is produced. The compositions produced according to this method can be used as colorless nail polishes or alternatively, as base coat and top coat formulations in conjunction with colored nail polishes. After the viscous solution is produced, a thixotropic agent, for example, stearalkonium hectorite, is added to the above-described mixture in conjunction with vigorous stirring (under strong shearing force with a Hoffmeyer industrial mixer) generally for a period of about at least one hour to produce a gelled mixture. In the last step, one or more pigments is added to the above gelled mixture to produce the rapid drying mixtures according to the present invention. The final composition produced by the method according to the present invention obtains a final static viscosity ranging from about 400 to about 1200 centipoises. Certain compositions of the present invention produced in this way including Bentone RSNC TM are storage stable and do not require the vigorous shaking that the prior art compositions often require after extended periods of storage.

The following examples are provided to illustrate the present invention and should not be construed to limit the scope of the invention of the present application in any way.

EXAMPLE 1

To demonstrate the effectiveness of the solvent compositions of the present invention in speeding the rate of drying of nail enamels, a commercially available red nail enamel sold under the trademark L'OREAL "Drumbeat" was obtained and the solvents distilled therefrom. The solvents were replaced by a solvent system containing 28.28 percent acetone in combination with additional solvents, including methylchloroform, ethyl acetate, toluene butyl acetate and isopropanol in the following weight ratios:

| Solvent | Weight Percent of Solvent in Solvent System (By Weight of Solvent) | Weight Percent of Solvent in Composition Based on Solids Weight Percent of 37.5% |
| --- | --- | --- |
| Acetone | 28.28% | 17.68% |
| Isopropanol | 2.02% | 1.26% |
| Ethyl Acetate | 39.94% | 24.96% |
| Toluene | 28.81% | 18.01% |
| Butyl Acetate | 0.74 | 0.46% |

| Solvent | Weight Percent of Solvent in Solvent System (By Weight of Solvent) | Weight Percent of Solvent in Composition Based on Solids Weight Percent of 37.5% |
| --- | --- | --- |
| Methyl Chloroform | 0.21 | 0.13% |

Results: The L'Oreal product "drumbeat" was evaporated to near dryness and the solvent system including 17.68% by weight acetone was added to the solids remaining after evaporation. The resulting suspension was shaken vigorously until a homogeneous suspension was realized. The viscosity was slightly thin, too thin to be commercialized. The drying time of the nail polish formulation was 70 seconds on plate glass. In comparison, the drying time of the L'Oreal product was greater than 4 minutes.

EXAMPLES 2-10

In the following examples, a number of solvent combinations containing at least 4.5% by weight of acetone were used to produce a number of nail enamel compositions using a standard base formulation. In each case, the drying time of the formulations was significantly less than 3 minutes.

| Non-Volatile Component (Solids) Component | Weight Percent of Final Composition |
| --- | --- |
| Primary Film-Forming Polymer Nitrocellulose RS ½ Sec. | 10.5% |
| Secondary Film-Forming Polymer Toluenesulfonamide formaldehyde Resin | 9.0 |
| Plasticizer | |
| Camphor | 0.4% |
| Dibutylphthalate | 4.1% |
| Bentone RSNC ™ Stearalkonium hectorite (25%) Nitrocellulose Camphor | 12.0% |

Procedure: To produce nail enamel compositions, the components listed above were added step-wise, in the order 1) primary film-forming polymer; 2) secondary film-forming polymer and 3) plasticizer to the below-described solvent systems. Each component was added and mixed until a homogeneous solution was produced. After the first three components were added, the Bentone RSNC ™ was added and the resulting mixture was mixed under high shearing force with a laboratory mixer for at least about 1 hour until a homogeneous gel was obtained. Pigments are added with further mixing. The resulting compositions were then "drawn down" on lineta cards to determine drying times. Drying times were determined by placing a cotton swab (Q-tips from Cheseborough Ponds, USA) on the surface. An absence of sticking of cotton swabs to the film was considered dry for purposes of the present invention. The drying times of the individual experiments are presented as indicated.

All formulations evidenced acceptable viscosities and an absence of streaking. To determine static viscosities, compositions were allowed to stand for at least 24 hours in a constant temperature bath at 25° C. Static viscosity tests were performed using a Brookfield LVF, spindle #3 at 12 RPM and 25° C. To determine static viscosity the dial reading was multiplied by a factor to determine approximate viscosity (e.g., 16×100=800 cps). It should be noted that the static viscosities were determined in the following experiments with a Brookfield LVF, spindle #3, but are defined in the general invention using a Brookfield RVF, spindle #3 as those of ordinary skill in the art would define them. Because access to a Brookfield RVF was not available, the static viscosities in the following invention are presented using the available Brookfield LVF instrumentation. The compositions of the present invention have acceptable viscosities.

Shaken viscosities were determined on a Brookfield LVF using Spindle #3 at 25° C.
  a) at 60 RPM. To determine viscosity dial reading was multiplied by a factor to determine approximate viscosity (e.g., 20×20=400 cps).
  b) at 6 RPM. To determine viscosity dial reading was multiplied by a factor to determine approximately (e.g., 5×200 =1000 cps).

Because of the nature of the viscosity determination, and may depend upon the amount of shaking done (variable), shaken viscosities are believed to be less reliable than are the static viscosities.

| Example 2 Solvent System #1 | |
| --- | --- |
| Solvent | Percent By Weight of Final Composition |
| Acetone | 18.1% |
| Isopropanol | 1.28 |
| Ethyl Acetate | 25.54% |
| N-Butyl Acetate | 0.64 |
| Methylchloroform | 18.44 |

Results: Composition including solids were formulated as described above using 64% by weight of solvent system #1 and 36% by weight of Non-Volatile Component as described above. Drying time on lineta cards (3 mm draw down) at an ambient temperature of 68.4° F. (20.2° C.) and a relative humidity of about 40% was 51 seconds. Drying time in a relative humidity of about 65-70% was 90 seconds. Static viscosity of the formulation was 1201 cps. Shaken viscosity at 60 RPM was 504 cps and at 6 RPM was 600 cps.

| Example 3 Solvent System #2 | |
| --- | --- |
| Solvent | Percent By Weight of Final Composition |
| Isopropanol | 1.28 |
| Ethyl Acetate | 25.54% |
| N-Butyl Acetate | 18.75% |
| Methylchloroform | 18.44 |

Results: Absence of acetone to determine effect of acetone on drying times. Composition including solids were formulated as described above using 64% by weight of solvent system #2 and 36% by weight of Non-Volatile Component as described above. Drying time on lineta cards (3 mm draw down) at an ambient temperature of 68.4° F. (20.2° C.) and a relative humidity of about 40% was 3 minutes and 17 seconds. Drying time in a relative humidity of about 65-70% is about 4.5 to 5 minutes. Static viscosity of the formulation was 970 cps. Shaken viscosity at 60 RPM was 626 cps and at 6 RPM was 720 cps.

Example 4
Solvent System #3

| Solvent | Percent By Weight of Final Composition |
| --- | --- |
| Isopropanol | 1.28 |
| Ethyl Acetate | 43.96% |
| N-Butyl Acetate | 18.75% |

Results: Absence of acetone and methylchloroform to determine effect of acetone and methylchloroform on drying times. Composition including solids were formulated as described above using 64% by weight of solvent system #3 and 36% by weight of Non-Volatile Component as described above. Drying time on lineta cards (3 mm draw down) at an ambient temperature of 68.4° F. (20.2° C.) and a relative humidity of about 40% was 3 minutes and 9 seconds. Drying time in a relative humidity of about 65–70% is about 4.5 to 5 minutes. Static viscosity of the formulation was 1950. Shaken viscosity at 60 RPM was 700 cps and at 6 RPM was 740 cps.

Example 5
Solvent System #4

| Solvent | Percent By Weight of Final Composition |
| --- | --- |
| Acetone | 18.11% |
| Isopropanol | 1.28 |
| Ethyl Acetate | 25.54% |
| N-Butyl Acetate | 0.51% |
| Methylchloroform | 0.13% |
| Methylene Chloride | 18.43% |

Results: Experiment to replace toluene with methylene chloride. Composition including solids were formulated as described above using 64% by weight of solvent system #4 and 36% by weight of Non-Volatile Component as described above. Viscosities were in acceptable range. Drying time on lineta cards (3 mm draw down) at an ambient temperature of 70° F. (21.5° C.) and a relative humidity of about 50% was 64 seconds. Drying time in a relative humidity of about 65–70% is significantly less than three minutes. Static viscosity of the formulation was 1750 cps. Shaken viscosity at 60 RPM was 936 cps and at 6 RPM was 2000 cps.

Example 6
Solvent System #5

| Solvent | Percent By Weight of Final Composition |
| --- | --- |
| Acetone | 18.11% |
| Isopropanol | 1.28 |
| Ethyl Acetate | 25.54% |
| N-Butyl Acetate | 0.51% |
| Methylchloroform | 0.13% |
| Methylethyl ketone | 18.43% |

Results: Experiment to replace toluene with methylethyl ketone. Composition including solids were formulated as described above using 64% by weight of solvent system #5 and 36% by weight of Non-Volatile Component as described above. Drying time on lineta cards (3 mm draw down) at an ambient temperature of 70° F. (21.5° C.) and a relative humidity of about 50% was 79 seconds. Drying time in a relative humidity of about 65–70% is significantly less than 3 minutes. Static viscosity of the formulation was 1470 cps. Shaken viscosity at 60 RPM was 624 cps and at 6 RPM was 1120 cps.

Example 7
Solvent System #6

| Solvent | Percent By Weight of Final Composition |
| --- | --- |
| Acetone | 18.11% |
| Isopropanol | 1.28 |
| Ethyl Acetate | 25.54% |
| N-Butyl Acetate | 0.51% |
| Methylchloroform | 0.13% |
| Hexane | 18.43% |

Results: Experiment to replace toluene with hexane. Composition including solids were formulated as described above using 64% by weight of solvent system #6 and 36% by weight of Non-Volatile Component as described above. Drying time on lineta cards (3 mm draw down) at an ambient temperature of 70° F. (21.5° C.) and a relative humidity of about 50% was 77 seconds. Drying time in a relative humidity of about 65–70% is significantly less than 3 minutes. Static viscosity of the formulation was 930 cps. Shaken viscosity at 60 RPM was 710 cps and at 6 RPM was 300 cps.

Example 8
Solvent System #7

| Solvent | Percent By Weight of Final Composition |
| --- | --- |
| Acetone | 18.11% |
| Isopropanol | 1.28 |
| Ethyl Acetate | 25.54% |
| N-Butyl Acetate | 0.51% |
| Methylchloroform | 0.13% |
| Cyclohexane | 18.43% |

Results: Experiment to replace toluene with cyclohexane. Composition including solids were formulated as described above using 64% by weight of solvent system #7 and 36% by weight of Non-Volatile Component as described above. Drying time on lineta cards (3 mm draw down) at an ambient temperature of 70° F. (21.5° C.) and a relative humidity of about 50% was 79 seconds. Drying time in a relative humidity of about 65–70% is significantly less than 3 minutes. Static viscosity of the formulation was 1120 cps. Shaken viscosity was 704 cps at 60 RPM and 400 cps at 6 RPM.

Example 9
Solvent System #8

| Solvent | Percent By Weight of Final Composition |
| --- | --- |
| Acetone | 4.5% |
| Isopropanol | 1.6 |
| Ethyl Acetate | 33.16% |
| Toluene | 23.95% |
| N-Butyl Acetate | 0.66% |
| Methylchloroform | 0.13% |

Results: Experiment to determine effect of reduced acetone. Composition including solids were formulated as described above using 64% by weight of solvent system #8 and 36% by weight of Non-Volatile Component as described above. Drying time on lineta cards (3 mm draw down) at an ambient temperature of 72.0° F. (23.0° C.) and a relative humidity of about 24% was 2 minutes. Drying time in a relative humidity of about 50–55% is about 3 minutes.

Example 10
Solvent System #9

| Solvent | Percent By Weight of Final Composition |
|---|---|
| Isopropanol | 1.3 |
| Ethyl Acetate | 25.5% |
| Toluene | 18.4% |
| N-Butyl Acetate | 0.5% |
| Methylchloroform | 0.1% |
| Methylene chloride | 18.2 |

Results: Experiment to determine effect of replacement of acetone with a solvent, methylene chloride, that has a much lower boiling point than acetone. Experiment was performed to determine if interaction of lower boiling solvents with other solvents in mixture was responsible for fast drying times. Composition position including solids were formulated as described above using 64% by weight of solvent system #9 and 36% by weight of Non-Volatile Component as described above. Drying time on lineta cards (3 mm draw down) at an ambient temperature of 64° F. (17.8° C.) and a relative humidity of about 37% was 3 minutes and 21 seconds. Drying time in a relative humidity of about 65–70% is about 5 minutes.

Example 11
Solvent System #10

| Solvent | Percent By Weight of Final Composition |
|---|---|
| Acetone | 18.2 |
| Isopropanol | 1.3 |
| Ethyl Acetate | 25.5% |
| Toluene | 18.4% |
| N-Butyl Acetate | 0.5% |
| Methylchloroform | 0.1% |

Results: Composition including solids are formulated as described above using 64% by weight of solvent system #10 and 36% by weight of Non-Volatile Component as described above. Drying time on lineta cards (3 mm draw down) at an ambient temperature of 72.7° F. (23.3° C.) and a relative humidity of about 55% is less than 60 seconds. Drying time in a relative humidity of about 65–70% is significantly less than 3 minutes.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

We claim:

1. A quick-dry composition for coating natural and synthetic nails of animals and humans comprising:
  a) about 5% to about 25% by weight of a primary film-forming polymer selected from the group consisting of cellulose acetate, cellulose acetate-butyrate, ethyl cellulose, nitrocellulose and mixtures thereof;
  b) about 4% to about 13% by weight of a secondary film-forming polymer;
  c) an amount of at least one plasticizer effective to provide acceptable flexibility of said composition on a human or synthetic nail after drying;
  d) about 0.025% to about 4.0% by weight of at least one pigment;
  e) a thixotropic agent included in said composition in an amount effective for enhancing the suspension of pigment; and
  f) an amount of acetone ranging from about 13% to about 25% by weight of said composition in combination with a mixture of solvents to produce a stable composition having a static viscosity ranging from about 400 to about 1200 centipoises, said composition drying to a film exhibiting a substantial absence of tack on a natural or synthetic nail within a period of less than about three minutes.

2. The composition according to claim 1 wherein said secondary film-forming polymer is selected from the group consisting of polyvinyl acetate, polyesters, acrylic resins, arylsulfonamide-formaldehyde resins and mixtures thereof.

3. The composition according to claim 2 wherein said primary film-forming polymer is nitrocellulose.

4. The composition according to claim 1 wherein said thixotropic agent is stearalkonium hectorite.

5. The composition according to claim 2 wherein said arylsulfonamide-formaldehyde resin is toluene sulfonamide formaldehyde.

6. The composition according to claim 1 wherein said plasticizer is selected from the group consisting of dibutylphthalate, camphor and mixtures thereof.

7. The composition according to claim 1 wherein said mixture of solvents is selected from the group consisting of ethyl acetate, methyl acetate, ethanol, isopropanol, n-butanol, n-butylacetate, toluene, xylene, amyl acetate and mixtures thereof.

8. The composition according to claim 4 wherein said mixture of solvents comprises at least two solvents selected from the group consisting of ethyl acetate, methyl acetate, ethanol, isopropanol, n-butanol, n-butylacetate, toluene, xylene and amyl acetate.

9. The composition according to claim 8 which includes methylethylketone.

10. The composition according to claim 9 wherein said primary film-forming polymer is nitrocellulose, said secondary film-forming polymer is toluene sulfonamide-formaldehyde resin, and said plasticizer is a mixture of dibutylphthalate and camphor.

11. A method for decreasing the drying time of a nail polish composition comprising about 7% to about 25% by weight of a primary film-forming polymer; about 3% to about 13% by weight of a secondary film-forming polymer; an amount of at least one plasticizer effective to provide said composition with acceptable flexibility on said nail; an amount of at least one organoclay thixotropic agent effective to produce gelling of said composition; about 0.025% to about 4.0% by weight of at least one pigment; and a mixture of solvents, said method comprising including in said composition an amount of acetone ranging from about 13% to about 35% by weight of said composition including acetone, said acetone and said mixture of solvents dissolving said primary and secondary film-forming polymers and said plasticizer, said composition including acetone further having a static viscosity ranging from about 400 to about 1200 centipoises, said composition including acetone drying on a natural or synthetic nail within about three minutes or less to a coating exhibiting a substantial absence of tack.

12. The method according to claim 11 wherein said primary film-forming polymer is nitrocellulose and said secondary film-forming polymer is toluene sulfonamide-formaldehyde resin.

13. The method according to claim 12 wherein said organoclay thixotropic agent is stearalkonium hectorite.

14. The method according to claim 11 wherein said mixture of solvents comprises at least two solvents selected from the group consisting of ethyl acetate, methyl acetate, ethanol, isopropanol, n-butanol, n-butylacetate, toluene, xylene and amyl acetate and mixtures thereof.

15. The method according to claim 11 wherein said mixture of solvents includes methylethyl ketone.

16. A method for decreasing the drying time of a nail polish composition comprising about 7% to about 25% by weight of a primary film-forming polymer; about 3% to about 13% by weight of a secondary film-forming polymer; an amount of at least one plasticizer effective to provide said composition with acceptable flexibility on said nail; an amount of at least one organoclay thixotropic agent effective to produce gelling of said composition; about 0.025% to about 4.0% by weight of at least one pigment; and a mixture of solvents including a wetting agent and at least one diluent solvent, said method comprising including in said composition an amount of acetone ranging from about 4.5% to about 35% by weight, said acetone and said mixture of solvents dissolving said primary and secondary film-forming polymers and said plasticizer, said composition including acetone further having a static viscosity ranging from about 400 to about 1200 centipoises, said composition including acetone drying on a natural or synthetic nail within about three minutes or less to a coating exhibiting a substantial absence of tack.

17. The method according to claim 16 wherein said primary film-forming polymer is nitrocellulose and said secondary film-forming polymer is toluene sulfonamide-formaldehyde resin.

18. The method according to claim 17 wherein said organoclay thixotropic agent is stearalkonium hectorite.

19. The method according to claim 18 wherein said mixture of solvents comprises at least two solvents selected from the group consisting of ethyl acetate, methyl acetate, ethanol, isopropanol, n-butanol, n-butylacetate, toluene, xylene and amyl acetate and mixtures thereof.

20. The method according to claim 19 wherein said mixture of solvents includes methylethyl ketone.

* * * * *